United States Patent

Machado et al.

[11] 3,972,692
[45] Aug. 3, 1976

[54] PROCESS FOR REMOVING ACID FROM HYDROCARBONS

[75] Inventors: Roberto L. Machado, Bernardsville; Benjamin Eisenberg, Morris Plains; George P. Baumann, Sparta, all of N.J.

[73] Assignee: Exxon Research and Engineering Company, Linden, N.J.

[22] Filed: Apr. 3, 1975

[21] Appl. No.: 564,707

[52] U.S. Cl. .................................... 55/23; 55/56; 55/68; 55/73
[51] Int. Cl.² ..................................... B01D 47/00
[58] Field of Search ............. 55/23, 36, 37, 40, 56, 55/73, 68

[56] References Cited
UNITED STATES PATENTS

| | | |
|---|---|---|
| 3,553,936 | 1/1971 | Little et al. ........................ 55/73 X |
| 3,664,091 | 5/1972 | Hegwer ............................. 55/73 X |
| 3,733,779 | 5/1973 | Bellisio et al. ....................... 55/73 |

Primary Examiner—John Adee
Attorney, Agent, or Firm—Marthe L. Gibbons

[57] ABSTRACT

Acidic gases, such as $H_2S$, COS, $CO_2$, and HCN are removed from a mixture of light hydrocarbons by first separating the mixture into a gas portion and a liquid portion. The gas portion is compressed, water washed and scrubbed with an absorbing solution prior to separating at least one hydrocarbon from other hydrocarbons in the mixture. The liquid portion is stripped of $H_2S$. The stripped vapors containing the stripped $H_2S$ may be recycled to the gas compression step.

6 Claims, 2 Drawing Figures

PROCESS FOR REMOVING ACID FROM HYDROCARBONS

BACKGROUND OF THE INVENTION

1. Field of the Invention

The present invention relates to a process for removing acidic gases such as $H_2S$, $COS$, $CO_2$ and $HCN$ from mixtures of lower boiling hydrocarbons.

2. Description of the Prior Art

Mixtures of light hydrocarbons, such as mixtures commonly known as light ends, which usually result from the thermal decomposition of high temperature petroleum refining operations are often recovered and separated into two or more hydrocarbon streams in a light ends treating operation, such as deethanizer and debutanizer towers. The acidic gases contained in these light ends cause corrosion of the light ends treating equipment.

Prior art technology typically consisted of compressing the gas portion and pumping the liquid portion of these light hydrocarbons and feeding them to a light ends fractionation system. Any acidic gases contained in the light ends were carried through the light ends fractionation towers and eventually removed from the separated products. In a typical light ends sequence, consisting of an absorber deethanizer tower followed by a dubutanizer, a portion of the acid gases would go to the overhead product from the deethanizer and be scrubbed out by a downstream scrubber using an amine solution or other absorbent. The remainder of the acid gases would typically concentrate on the overhead product of the debutanizer, usually a $C_3/C_4$ LPG stream, and be removed by liquid/liquid treating with an amine and/or caustic solution.

The presence of corrosive agents in the light ends towers in such schemes as described above has been known to cause severe corrosion of the fractionating vessels and associated equipment. Also, the presence of HCN, which reacts irreversibly with the amine to form degradation products, has resulted in large amine losses.

The present invention provides a process which relieves both of these conditions by (1) placing the acid gas removal system upstream of the light ends towers and (2) placing a water scrubber to remove the bulk of the HCN upstream of the amine tower.

A method has now been found whereby the acidic gases are removed from the light ends prior to processing the light ends in light ends recovery equipment.

SUMMARY OF THE INVENTION

In accordance with the invention there is provided, in a process for separating at least one hydrocarbon from other hydrocarbons in a mixture comprising light hydrocarbons and acidic gases, the improvement which comprises removing said acidic gases from said mixture prior to said hydrocarbon separation step by the steps which comprise:

a. separating said mixture into a gaseous portion and a liquid portion;

b. subjecting said gaseous portion to compression, water washing and scrubbing with an aqueous absorbing solution; and c. subjecting the liquid portion to stripping to remove at least a portion of the hydrogen sulfide therefrom and to produce a hydrogen sulfide-containing effluent. If desired the hydrogen sulfide-containing effluent may be recycled to the gas compression step.

DESCRIPTION OF THE PREFERRED EMBODIMENT

Figure 1:
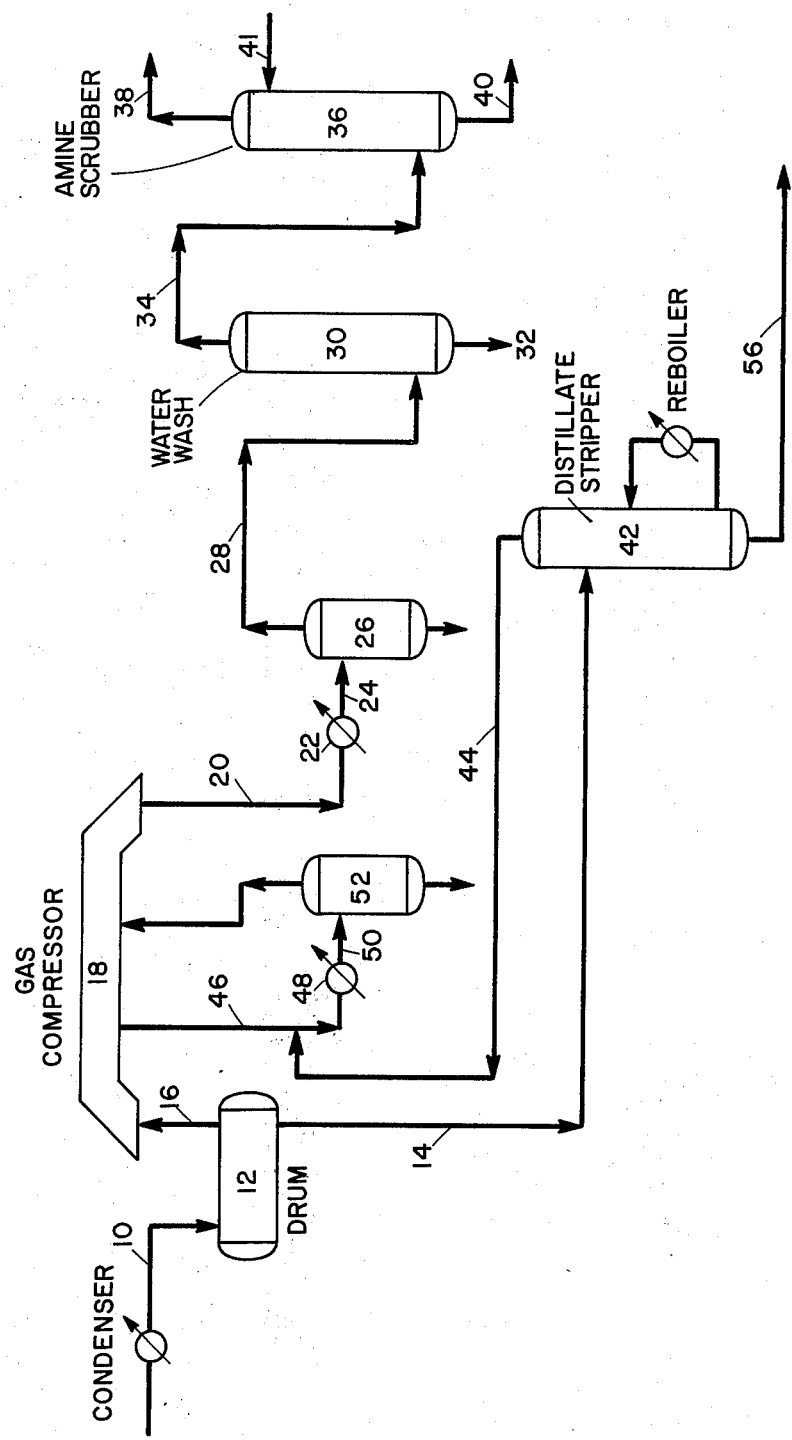
FIG. 1 is a schematic flow plan of one embodiment of the invention.

Referring to FIG. 1, a mixture of light hydrocarbons containing acidic gas contaminants, such as $H_2S$, $CO_2$ and HCN, is passed via line 10 into drum 12. Suitable mixtures include mixtures having hydrocarbon components boiling (at atmospheric pressure) in the range between Cl, and 400°F. The major source of light hydrocarbons is the thermal decomposition of high temperature petroleum refining operation. The mixture of light hydrocarbons may be, for example, the overhead vapor of a coker products fractionator or the overhead vapor of a catalytic cracking products fractionator, typical compositions of which are tabulated below.

| Stream: Constituent | Coker Fractionator Overhead Mole % | Catalytic Cracking Fractionator Overhead Mole % |
|---|---|---|
| $H_2$ | 10.58 | 2.20 |
| $C_1$ | 27.76 | 11.78 |
| $C_2$ | 15.68 | 9.58 |
| $C_3$ | 10.05 | 14.22 |
| $C_4$ | 5.35 | 12.69 |
| $C_5+$ | 13.76 | 41.49 |
| $H_2O$ | 7.22 | 4.31 |
| $H_2S$ | 4.12 | 1.78 |
| CO | 1.50 | — |
| $CO_2$ | 0.50 | — |
| HCN | 0.01 | — |
| Inerts | 3.47 | 1.95 |
| | 100.00 | 100.00 |

In drum 12, the mixture is separated into a liquid portion removed by line 14 and a gaseous portion removed by line 16. The gas portion is passed to a gas compressor 18, removed via line 20 and passed through aftercooler 22, then through line 24 into aftercooler drum 26 from where it is passed via line 28 into a conventional water washing stage in tower 30. Foul water is removed from water washing tower 30 via line 32. The water washed portion is removed via line 34 and sent to tower 36 in which the water washed portion is subjected to a conventional scrubbing stage with an absorbing aqueous solution, such as an amine solution for removal of carbon dioxide and hydrogen sulfide. Typical prior art amine scrubbing processes are described in U.S. Pat No. 3,144,301, and in U.S. Pat. No. 3,851,041, the teachings of which are hereby incorporated by reference.

The scrubbed gas is removed from the absorption tower 36 by line 38. The absorbent-rich solution is removed via line 40. The absorbent-lean solution enters the absorption tower via line 41. The scrubbed gas removed via line 38, which is a gas containing a negligible amount of acidic contaminants, is suitable as feed to a light ends recovery operation such as a deethanizing stage.

Returning to drum 12, the liquid portion is passed via line 14 to a reboiled stripping tower 42. Hydrogen sulfide and lighter components are removed from tower 42 by line 44 and, if desired, recycled to gas compressor 18 via line 46, intercooler 48, line 50, interstage drum 52 and line 54. The stripped liquid portion is removed from stripper 42 via line 56. The stripped liquid containing a negligible amount of acidic components is suitable as feed to a light ends recovery process, such as a deethanizing stage.

The following example is presented to illustrate the invention.

EXAMPLE

Figure 2:
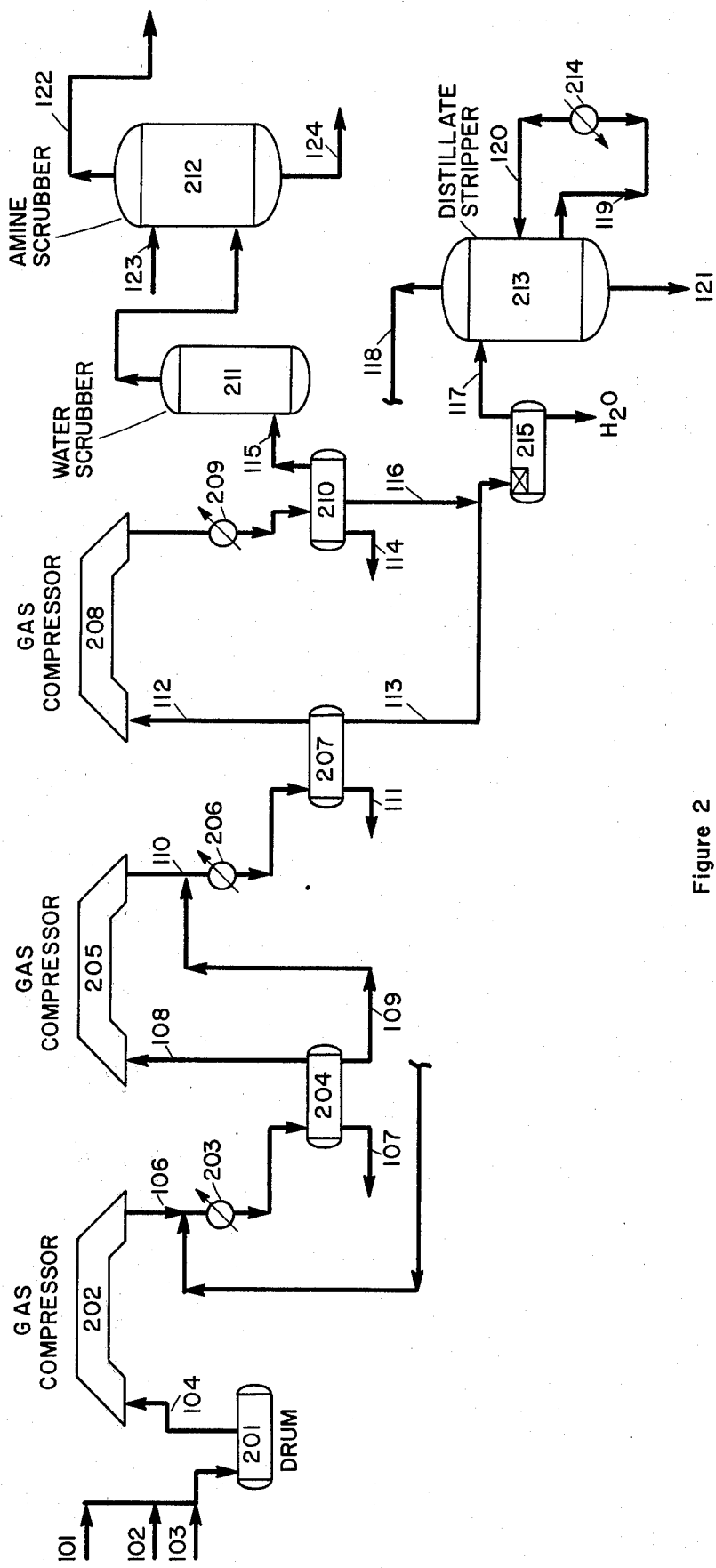
FIG. 2 is a schematic flow plan of another embodiment of the invention.

As illustrative example, the stream compositions and conditions of a specific embodiment of the scheme shown in FIG. 2 are given in Table II. Referring to FIG. 2, a vacuum pipestill overhead gas (stream 101), a coker naphtha hydrofiner stripper overhead (stream 102) and a coker fractionator vapor distillate (stream 103) are combined and passed to a coker fractionator distillate drum (201). The overhead gas from the coker fractionator distillate drum is compressed in a three-stage centrifugal gas compressor (202, 205, 208). In Table I are listed various stages indicated in FIG. 2 and their corresponding numerals.

TABLE I

| Numeral | Stages |
|---|---|
| 203 | first stage intercooler |
| 204 | first stage drum |
| 206 | second stage intercooler |
| 207 | second stage drum |
| 210 | third stage drum |
| 211 | water scrubber |
| 212 | amine scrubber |
| 213 | distillate stripper |
| 214 | reboiler |
| 215 | drum |

TABLE II

| Stream No. | 101 | 102 | 103 | 104 | 105 | 106 | 107 | 108 |
|---|---|---|---|---|---|---|---|---|
| Stream Name | Vacuum P/S Overhead | Coker Naphtha N/F Stripper Overhead Vapor | Coker Fractionator Vapor Dist. | Compressor 1st Stage Inlet | Coker Fractionator Liquid Distillate | 1st Stage Intercooler Feed | 1st Stage K.O. Drum Water Cond. | Compressor 2nd Stage Inlet |
| Conditions | Vapor | Vapor | Vapor | Vapor | LIquid | Vapor | Liquid | Liquid | Vapor |
| Pressure, Psig | 2 | 75 | 2 | 1 | 55 | 30 | 30 | 25 | 25 |
| Temperature, °F | 110 | 135 | 110 | 110 | 110 | 183 | 183 | 100 | 100 |
| Composition, Moles/Hr. | | | | | | | | |
| $H_2$ | — | 7.1 | 293.9 | 301.0 | — | 301.3 | — | — | 301.3 |
| $H_2S$ | 8.2 | 11.0 | 114.3 | 133.5 | 0.3 | 141.2 | 0.2 | — | 139.6 |
| $C_1$ | — | 5.3 | 770.7 | 776.0 | 0.2 | 781.0 | 0.2 | — | 780.2 |
| $C_2^=$ | — | — | 147.7 | 147.7 | 0.2 | 151.1 | 0.1 | — | 150.5 |
| $C_2$ | 37.7 | — | 287.1 | 324.8 | 0.4 | 334.4 | 0.3 | — | 332.7 |
| $C_3^=$ | — | — | 151.6 | 151.6 | 0.6 | 164.3 | 0.4 | — | 161.9 |
| $C_3$ | — | — | 126.5 | 126.5 | 0.5 | 138.4 | 0.4 | — | 136.1 |
| $iC_4$ | — | — | 6.7 | 6.7 | 0.1 | 7.5 | — | — | 7.1 |
| $C_4^=$ | — | 1.5 | 93.7 | 95.2 | 1.3 | 105.5 | 0.6 | — | 100.0 |
| $nC_4$ | — | 0.8 | 39.0 | 39.8 | 0.5 | 43.4 | 0.3 | — | 40.8 |
| $C_4^=$ | — | — | 7.2 | 7.2 | 0.1 | 7.6 | 0.1 | — | 6.9 |
| $C_5+$ | — | 2.0 | 232.3 | 234.3 | 149.8 | 316.2 | 72.8 | — | 137.3 |
| $H_2O$ | 3.5 | — | 200.6 | 204.1 | — | 204.1 | — | 143.0 | 61.1 |
| CO | — | — | 41.8 | 41.8 | — | 41.9 | — | — | 41.9 |
| $N_2$ | 9.0 | — | 96.5 | 105.5 | — | 105.6 | — | — | 105.6 |
| $CO_2$ | — | — | 14.3 | 14.3 | — | 14.6 | — | — | 14.6 |

| Stream No. | 109 | 110 | 111 | 112 | 113 | 114 | 115 | 116 |
|---|---|---|---|---|---|---|---|---|
| Stream Name | 1st Stage K.O. Drum Hydrocarbon Condensate | 2nd Stage Intercooler Feed | 2nd Stage K.O. Drum Water Cond. | Compressor 3rd Stage Inlet | 2nd Stage K.O. Drum Hydrocarbon Condensate | 3rd Stage K.O. Drum Water Cond. | Vapor to Water Scrubber | 3rd Stage K.O. Drum Hydrocarbon Condensate |
| Conditions | Liquid | Vapor | Liquid | Liquid | Vapor | Liquid | Liquid | Vapor | Liquid |
| Pressure,Psig | 25 | 84 | 84 | 80 | 80 | 80 | 230 | 230 | 230 |
| Temperature, °F | 100 | 170 | 170 | 100 | 100 | 100 | 100 | 100 | 100 |
| Composition, Moles/Hr. | | | | | | | | |
| $H_2$ | — | 301.2 | 0.1 | — | 301.1 | 0.2 | — | 301.0 | 0.1 |
| $H_2S$ | 1.8 | 139.5 | 1.9 | — | 135.4 | 6.0 | — | 133.8 | 1.6 |
| $C_1$ | 1.0 | 779.4 | 1.8 | — | 777.5 | 3.7 | — | 776.2 | 1.3 |
| $C_2^=$ | 0.7 | 150.2 | 1.0 | — | 148.7 | 2.5 | — | 147.9 | 0.8 |
| $C_2$ | 2.0 | 332.0 | 2.7 | — | 327.5 | 7.2 | — | 325.2 | 2.3 |
| $C_3^=$ | 2.8 | 161.6 | 3.1 | — | 155.0 | 9.7 | — | 152.1 | 2.9 |
| $C_3$ | 2.7 | 135.9 | 2.9 | — | 129.5 | 9.3 | — | 126.7 | 2.8 |
| $iC_4$ | 0.4 | 7.2 | 0.3 | — | 6.4 | 1.1 | — | 6.1 | 0.3 |
| $C_4^=$ | 6.1 | 101.0 | 5.1 | — | 87.6 | 18.5 | — | 82.6 | 5.0 |
| $nC_4$ | 2.9 | 41.3 | 2.4 | — | 35.0 | 8.7 | — | 32.7 | 2.3 |
| $C_4^=$ | 0.8 | 7.1 | 0.6 | — | 5.5 | 2.2 | — | 5.0 | 0.5 |
| $C_5+$ | 251.7 | 185.0 | 204.0 | — | 74.4 | 314.6 | — | 49.8 | 24.6 |
| $H_2O$ | — | 61.1 | — | 36.9 | 24.2 | — | 15.2 | 9.0 | — |
| CO | — | 41.9 | — | — | 41.8 | 0.1 | — | 41.8 | — |
| $N_2$ | — | 105.6 | — | — | 105.5 | 0.1 | — | 105.5 | — |
| $CO_2$ | — | 14.6 | — | — | 14.4 | 0.2 | — | 14.3 | 0.1 |

| Stream No. | 117 | 118 | 119 | 120 | 121 | 122 | 123 | 124 |
|---|---|---|---|---|---|---|---|---|
| Stream Name | Distillate Stripper Feed | Distillate Stripper Overhead | Distillate Stripper Reboiler Feed | Distillate Stripper Reboiler Return | Distillate Stripper Bottoms | MEA¹ Scrubber Overhead | Lean MEA | Rich MEA |

TABLE II-continued

| Conditions | Vapor | Liquid | Vapor | Liquid | Vapor | Liquid | Liquid | Vapor | Liquid | Liquid |
|---|---|---|---|---|---|---|---|---|---|---|
| Pressure, Psig | 50 | 50 | 50 | 52 | 52 | 52 | 52 | 226 | 250 | 230 |
| Temperature, °F | 98 | 98 | 123 | 212 | 272 | 272 | 272 | 120 | 120 | 146 |
| Composition, Moles/Hr. | | | | | | | | | | |
| $H_2$ | 0.3 | — | 0.3 | — | — | — | — | 300.9 | — | — |
| $H_2S$ | 0.8 | 6.8 | 7.6 | — | — | — | — | — | 23.0 | 156.8 |
| $C_1$ | 2.6 | 2.4 | 5.0 | — | — | — | — | 776.2 | — | — |
| $C_2=$ | 0.8 | 2.5 | 3.3 | — | — | — | — | 147.9 | — | — |
| $C_2$ | 1.7 | 7.8 | 9.5 | — | — | — | — | 325.2 | — | — |
| $C_3=$ | 0.9 | 11.7 | 12.5 | 1.1 | 1.0 | 0.1 | 0.1 | 152.1 | — | — |
| $C_3$ | 0.8 | 11.3 | 11.8 | 2.0 | 1.7 | 0.3 | 0.3 | 126.7 | — | — |
| $iC_4$ | — | 1.4 | 0.7 | 3.3 | 2.6 | 0.7 | 0.7 | 6.1 | — | — |
| $C_4=$ | 0.5 | 23.0 | 9.6 | 62.4 | 48.5 | 15.9 | 13.9 | 82.6 | — | — |
| $nC_4$ | 0.2 | 10.8 | 3.4 | 31.6 | 24.0 | 7.6 | 7.6 | 32.8 | — | — |
| $C_4=$ | — | 2.7 | 0.4 | 8.0 | 5.7 | 2.3 | 2.3 | 5.0 | — | — |
| $C_5+$ | 0.3 | 338.9 | 4.9 | 472.7 | 138.4 | 334.3 | 334.3 | 49.8 | — | — |
| $H_2O$ | — | — | — | — | — | — | — | 14.8 | 6244.0 | 6238.2 |
| CO | 0.1 | — | 0.1 | — | — | — | — | 41.8 | — | — |
| $N_2$ | 0.1 | — | 0.1 | — | — | — | — | 105.5 | — | — |
| $CO_2$ | 0.1 | 0.2 | 0.3 | — | — | — | — | — | — | 14.3 |
| MEA | | | | | | | | | 460.0 | 460.0 |

[1] MEA — monoethanolamine

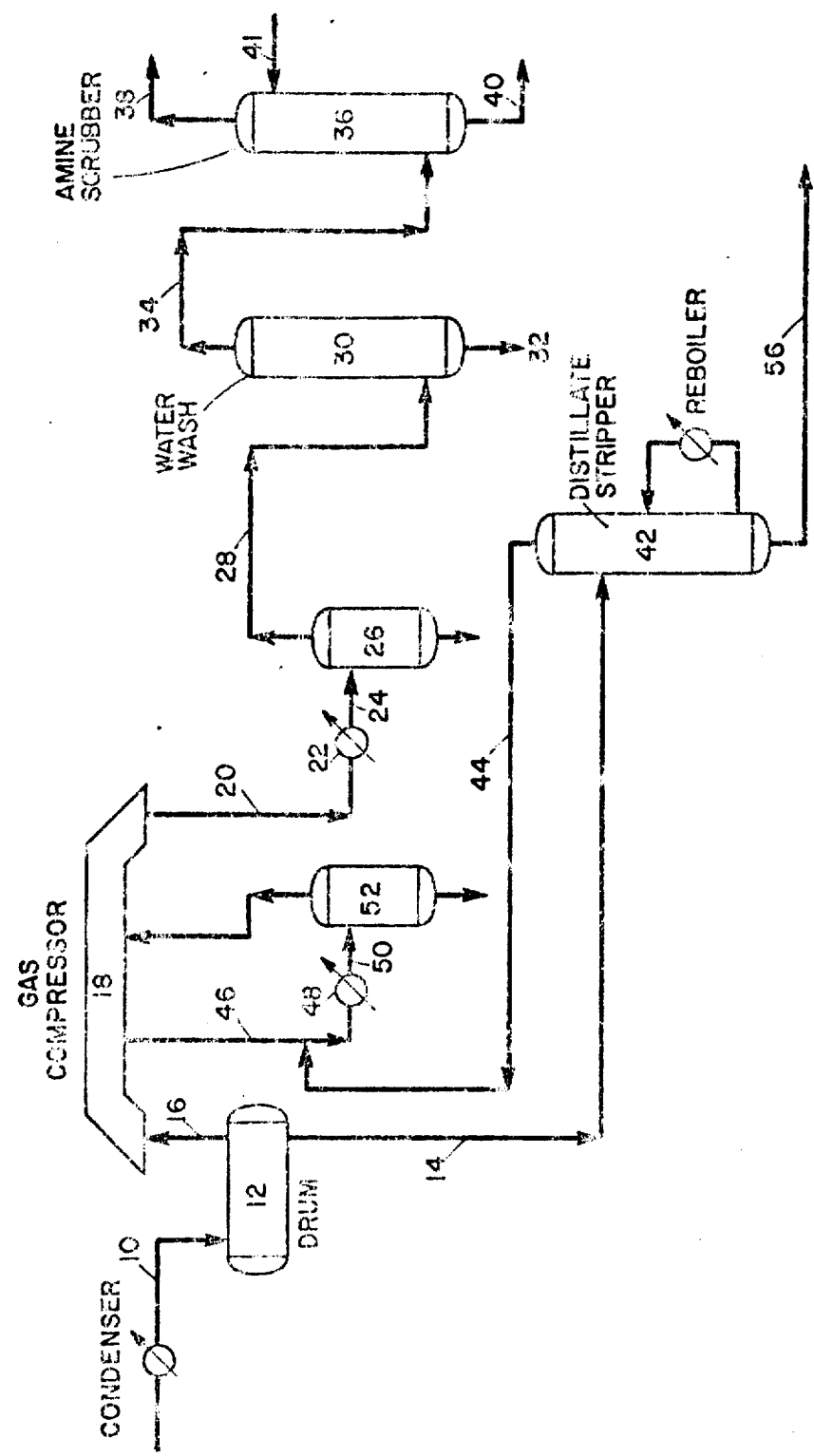

What is claimed is:

1. In a process for separating at least one hydrocarbon from other hydrocarbons in a mixture comprising light hydrocarbons and acidic gases, the improvement which comprises removing said acidic gases from said mixture prior to said hydrocarbon separation step by the steps which comprise:
    a. separating said mixture into a gaseous portion and a liquid portion;
    b. subjecting said gaseous portion to compression, water washing, and scrubbing with an aqueous absorbing solution; and
    c. subjecting the liquid portion to stripping to remove at least a portion of the hydrogen sulfide therefrom and produce a hydrogen sulfide-containing effluent.

2. The process of claim 1, wherein the hydrogen sulfide-containing effluent is recycled to said gas compression step.

3. The process of claim 1, wherein said acidic gases are selected from the group consisting of $H_2S$, $CO_2$, COS, HCN and mixtures thereof.

4. The process of claim 1, wherein said mixture of light hydrocarbons comprises hydrocarbons boiling in the range between Cl and 400°F.

5. The process of claim 1, wherein said mixture of light hydrocarbons comprises the overhead vapor of a coking reaction products fractionator.

6. The process of claim 1, wherein said mixture of light hydrocarbons comprises the overhead vapor of a catalytic cracking reaction products fractionator.

* * * * *

UNITED STATES PATENT OFFICE
CERTIFICATE OF CORRECTION

Patent No. 3,972,692                         Dated   August 3, 1976

Inventor(s) Roberto L. Machado et al.

It is certified that error appears in the above-identified patent and that said Letters Patent are hereby corrected as shown below:

On the cover sheet the illustrated drawing should appear as shown on the attached sheet.

Signed and Sealed this

Nineteenth Day of October 1976

[SEAL]

Attest:

RUTH C. MASON
*Attesting Officer*

C. MARSHALL DANN
*Commissioner of Patents and Trademarks*